(12) United States Patent
Bauer et al.

(10) Patent No.: US 7,718,599 B2
(45) Date of Patent: May 18, 2010

(54) PHARMACEUTICAL ADMINISTRATION FORM FOR PEPTIDES, PROCESS FOR ITS PREPARATION, AND USE

(75) Inventors: Horst Bauer, Hersbruck (DE); Michael Damm, Rödermark (DE); Werner Sarlikiotis, Peania (GR)

(73) Assignee: AEterna Zentaris GmbH, Frankfurt (DE)

( * ) Notice: Subject to any disclaimer, the term of this patent is extended or adjusted under 35 U.S.C. 154(b) by 0 days.

(21) Appl. No.: 09/861,009

(22) Filed: May 18, 2001

(65) Prior Publication Data

US 2002/0039996 A1 Apr. 4, 2002

(30) Foreign Application Priority Data

May 18, 2000 (DE) ................................ 100 24 451

(51) Int. Cl.
  *A61K 38/00* (2006.01)
  *A61K 51/00* (2006.01)
  *B01A 19/00* (2006.01)
(52) U.S. Cl. .................... 514/2; 424/1.69; 514/800; 422/40
(58) Field of Classification Search .............. 514/2
  See application file for complete search history.

(56) References Cited

U.S. PATENT DOCUMENTS

| | | | |
|---|---|---|---|
| 4,565,804 A | | 1/1986 | Rivier et al. |
| 4,800,191 A | | 1/1989 | Schally et al. |
| 5,541,159 A | * | 7/1996 | Albert et al. ............. 514/8 |
| 5,643,878 A | * | 7/1997 | Bold et al. ............. 514/19 |
| 5,663,145 A | | 9/1997 | Engel |
| 5,723,269 A | | 3/1998 | Akagi et al. |
| 5,942,493 A | | 8/1999 | Kutscher et al. |
| 6,054,555 A | | 4/2000 | Engel et al. |
| 6,087,324 A | | 7/2000 | Igari et al. |
| 6,180,608 B1 | | 1/2001 | Gefter et al. |
| 6,245,346 B1 | | 6/2001 | Rothen-Weinhold et al. |
| 6,346,274 B1 | | 2/2002 | Koll et al. |
| 6,416,740 B1 | * | 7/2002 | Unger ............. 424/484 |
| 6,627,609 B1 | | 9/2003 | Bernd et al. |
| 6,716,817 B1 | | 4/2004 | Engel |
| 6,828,415 B2 | | 12/2004 | Engel |
| 6,863,891 B2 | | 3/2005 | Engel |
| 6,867,191 B2 | | 3/2005 | Engel |
| 2001/0018072 A1 | * | 8/2001 | Unger ............. 424/484 |
| 2002/0099018 A1 | | 7/2002 | Engel et al. |
| 2002/0103113 A1 | | 8/2002 | Engel |
| 2002/0198186 A1 | | 12/2002 | Engel |
| 2003/0096839 A1 | * | 5/2003 | Floyd et al. ............. 514/307 |
| 2003/0108624 A1 | * | 6/2003 | Kosbab ............. 424/729 |
| 2005/0124546 A1 | | 6/2005 | Engel |

FOREIGN PATENT DOCUMENTS

| | | | |
|---|---|---|---|
| AU | 671881 | | 9/1996 |
| CA | 2115943 | * | 8/1994 |
| CN | 1112019 | | 11/1995 |
| CN | 1249691 | | 4/2000 |
| DE | 141 996 | | 4/1980 |
| DE | 4305225 | | 8/1994 |
| DE | 4342091 | | 6/1995 |
| DE | 199 11 771 A1 | | 9/2000 |
| EP | 0 175 506 A2 | | 3/1986 |
| EP | 0 611 572 B1 | | 6/2000 |
| JP | 06321800 A | | 11/1994 |
| WO | WO 96/07398 A2 | | 3/1996 |
| WO | WO 9607399 | | 3/1996 |
| WO | WO 9741836 | | 11/1997 |
| WO | WO 9825642 | | 6/1998 |
| WO | WO 9832423 | | 7/1998 |
| WO | WO 9842381 | | 10/1998 |

OTHER PUBLICATIONS

Rongières-Bertrand et al. Revival of the natural cycles in in-vitro fertilization with the use of a new gonadotrophin-releasing hormone antagonist (Cetrorelix): a pilot study with minimal stimulation. Hum Reprod. Mar. 1999;14(3):683-8.*
Michael F. Powell, Lynda M. Sanders, Alan Rogerson, and Vicki Si, Parenteral Peptide Formulations: Chemical and Physical Properties of Native Luteinizing Hormone-Releasing Hormone(LHRH) and Hydrophobic Analogues in Aqueous Solution, Pharmaceutical Research, vol. 8, No. 10, 1991.
M. Dathe, K. Gast, D. Zirwer, H. Welfle and B. Mehlis, Insulin Aggregation in Solution, Int. J. Peptide Protein Res. 36, 1990, 344-349.
Cyclodextrins in Drug Formulations: Part I, Feb. 1991 Pharmaceutical Technology International, pp. 15-22.
Melenteva Ga et. al. Pharmaceutical Chemistry Moscow "Medicine", 1993, p. 8-9.

* cited by examiner

*Primary Examiner*—Maury Audet
(74) *Attorney, Agent, or Firm*—Goodwin Procter LLP

(57) ABSTRACT

The invention relates to pharmaceutical compositions suitable for parenteral administration comprising, peptides in the form of acetate, gluconate, glucuronate, lactate, citrate, ascorbate, benzoate or phosphate salts in dissolved or dispersed form and at least one of the acids for forming the salts in free acid form.

17 Claims, No Drawings

PHARMACEUTICAL ADMINISTRATION FORM FOR PEPTIDES, PROCESS FOR ITS PREPARATION, AND USE

The invention relates to novel galenic forms for the parenteral administration of peptides prone to aggregation, in particular of LHRH analogues or LHRH antagonists and agonists, and processes for their preparation, and use.

EP 0 299 402 discloses the use of pharmaceutically active decapeptides such as SB-030, SB-075 (cetrorelix) and SB-088 in the form of their pharmaceutically acceptable, non-toxic acid addition salts such as hydrochlorides, hydrobromides, sulphates, phosphates, fumarates, gluconates, tannates, maleates, acetates, citrates, benzoates, succinates, alginates, pamoates, ascorbates and tartrates etc.

JP 06321800-A furthermore discloses a lyophilized peptide or protein preparation which contains gluconate salts as stabilizers. In one example, the solution contains 2.5% of magnesium gluconate, the active compounds described being, inter alia, vasopressin, LHRH and insulin.

It is known from the literature, inter alia from Powell, M. F., Pharmaceutical Research, 1258-1263(8) 1991; Dathe M. Int. J. Peptide Protein Res. 344-349(36) 1990, and Szejtli, J. Pharmaceutical Technology International 16-22, 1991, that oligopeptides, namely particularly those having a terminal acid amide function, are prone to gel formation.

EP 0 611 572 describes a preparation process for a lyophilizate of a peptide having 3-15 amino acids, according to which 100-10,000 parts by weight of the peptide are dissolved in acetic acid and treated with bulking agents such as mannitol, and then lyophilized in order to obtain a sterile-filtered lyophilizate of the peptide and to avoid gel formation.

DE A 195 42 873 describes pharmaceutical administration forms of complicated composition in the form of microparticles, according to which an ABA triblock copolymer is used whose A block is a polymer of milk [sic] and glycolic acid and whose B polymer is a polyethylene glycol chain, together with an additive from the group consisting of the serum proteins, polyamino acids, cyclodextrins, cyclodextrin derivatives, saccharides, amino sugars, amino acids, detergents or carboxylic acids and mixtures of these substances. After inclusion of small or aggregation-sensitive amounts of polypeptide, the microparticles described should also release the polypeptide continuously over a relatively long period.

DD 141 996 describes the preparation of pharmaceutical forms of native LHRH which are stable over a relatively long period and comply with the requirements for a parenterally administerable preparation. The key point here is the improvement in the shelf life of these preparations (page 2, lines 19-23). No statement is made about the filterability of the solutions. Moreover, to improve the shelf life buffer substances (also acetic acid) are also employed to establish a pH range of pH 3.5-6.5. The problem of preparing sterile lyophilizates from gel-forming peptide salts is not solved there.

EP 0 175 506 treats an aqueous solution of the peptide with 1N acetic acid and then lyophilizes it in order to obtain the acetate salt of the peptide. The subject of this application is thus the synthesis of the peptide salts.

However, it has been shown that in the case of the known acetate salts of the peptides prone to aggregation, such as the LHRH antagonists, the preparation of sterile solutions for parenteral administration by means of filtration, especially at high concentrations, is indeed possible, but aggregates can form shortly before injection after the dissolution of the lyophilizate. The aggregates then lead to a concentration-dependent lowering of the bioavailability from a peptide concentration of 0.5 mg/ml.

The problem mentioned occurs not only with injection solutions which are administered for the purpose of rapid release of active compound, but is also observed with injection preparations which exhibit delayed release. Thus peptides, incorporated in matrices which should control the release of active compound, can have an undesirably low release on account of their proneness to aggregation. Thus the bioavailability is also lowered here.

Starting from the fact that the preferred administration of pharmaceutically active peptides such as LHRH agonists and antagonists, for example antarelix and cetrorelix, is the parenteral pharmaceutical form, a need exists for the provision of stable injection preparations having acceptable bioavailability, which can be conveniently prepared, sterile-filtered and formulated. This applies in particular to injection preparations in the form of reconstituted lyophilizates of soluble peptide salts and to microparticles, microcapsules or implants.

This is all the more of importance in consideration of the varied areas of use of the LHRH antagonists, which are becoming more and more known.

A wider selection of parenterally, in particular subcutaneously, injectable, stable peptide solutions is desirable in view of the rapidly growing indication areas of this class of substance.

Pharmaceutical administration forms suitable for parenteral administration, which contain peptides prone to aggregation in dissolved or dispersed form, have now been developed which are distinguished in that the peptides are present in the form of their acetate, gluconate, glucuronate, lactate, citrates, ascorbate, benzoate or phosphate salts and that these administration forms can additionally contain one of the just-mentioned acids as free acids, and, if appropriate, further additives and excipients from the class consisting of the acids, surface-active substances, polymers, lipids or sugars.

These pharmaceutical administration forms can be present in dissolved or dispersed form in water or in aqueous solvent mixtures.

According to a further embodiment of the invention, the pharmaceutical administration forms can also be present in dissolved or dispersed form in a physiologically tolerable oil, preferably medium-chain triglycerides (neutral oils, Miglyol®) or castor oil, sesame oil, cottonseed oil, maize oil, peanut oil, olive oil or in mixtures of such oils.

The peptides employed are the LHRH antagonists antide, A-75998, ganirelix and Nal-Glu antagonist, but in particular cetrorelix, antarelix and the antagonists according to the U.S. Pat. No. 5,942,493 and DE 19911771.3.

Acids employed in the excipient function are gluconic acid, glucuronic acid, galacturonic acid, glucaric acid, citric acid, ascorbic acid and amino acids.

It is thus possible to suppress the aggregation of the peptide and thus to fulfil the requirements for a preparation having good bioavailability, and thus to enrich the pharmaceutical wealth and to do so with efficient galenic technology.

It has further surprisingly been found that by the addition of gluconic, glucuronic, citric, lactic or ascorbic acid, the stability of various cetrorelix salts is moreover considerably improved.

According to the invention, the preparation and formulation of sterile-filtered, stable preparations is thus possible without problems.

It is additionally advantageous to add suitable excipients. These excipients can be acids, surface-active substances, polymers, lipids or sugars. Examples of acids are gluconic acid, glucuronic acid, galacturonic acid, glucaric acid, lactic and citric acid, ascorbic acid and amino acids. Surface-active substances employed can be polyethylene glycol 12-(hydroxy)stearate (Solutol®), polyoxyethylene ricinoleate (Cremophor®), polysorbates, poloxamers, phospholipids, lecithins or benzalkonium chloride. Suitable polymers are albumins, polyethylene glycols, cellulose derivatives, starch derivatives or polyvinylpyrrolidone. Examples of sugars are cyclodextrins and cyclodextrin derivatives. 'Chaotropic' substances such as urea can also serve as additives and/or excipients.

The area of use of the preparations according to the invention is in particular in the prevention and therapy of all sex hormone-dependent conditions and diseases which can be influenced by LHRH analogues, i.e. LHRH agonists and LHRH antagonists. Those to be emphasized here are:

benign prostate hyperplasia, carcinoma of the prostate, precocious puberty, hirsutism, endometrial hyperplasia and its accompanying symptoms, endometrial carcinoma, in-vitro fertilization (IVF/COS/ART), contraception, premenstrual syndrome (PMS), uterine myomatosis, breast cancer, tubal obstruction (PTO), ovarian cancer, carcinoma of the uterus. The following substances are particularly preferred as LHRH antagonists for the composition according to the invention:

cetrorelix, antarelix, antide, A-75998, ganirelix, the Nal-Glu antagonist, and LHRH antagonists according to the U.S. Pat No. 5,942,493 and DE 19911771.3.

The LHRH antagonists according to the patents U.S. Pat. No. 5,942,493 and DE 19911771.3 are compounds of the following general formulas I, V and VII and the salts thereof with pharmaceutically acceptable acids

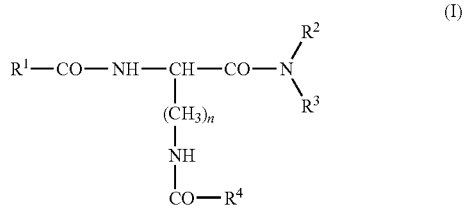
(I)

in which n is the number 3 or 4, $R^1$ is an alkyl group, an alkyloxy group, an aryl group, a heteroaryl group, an aralkyl group, a heteroaralkyl group, an aralkyloxy group or a heteroaralkyloxy group, in each case unsubstituted or substituted, $R^2$ and $R^3$ independently of one another are each a hydrogen atom, an alkyl group, an aralkyl group or a heteroaralkyl group, in each case unsubstituted or substituted, where the substitution can in turn consist of an aryl group or heteroaryl group, or —$NR^2R^3$ is an amino acid group, and $R^4$ is a group having the formula (II)

—$(CH_2)_p$—CO—$NR^5R^6$ (II)

in which p is an integer from 1 to 4, $R^5$ is hydrogen or an alkyl group and $R^6$ is an unsubstituted or substituted aryl or heteroaryl group, or $R^4$ is a ring of the general formula (III)

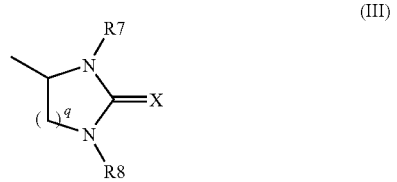
(III)

in which q is the number 1 or 2, $R^7$ is a hydrogen atom or an alkyl group, $R^8$ is a hydrogen atom or an alkyl group and X is an oxygen or sulphur atom, where the aromatic or heteroaromatic radicals can be partially or completely hydrogenated and chiral carbon atoms can have the R- or S-configuration, and its salts with pharmaceutically acceptable acids;

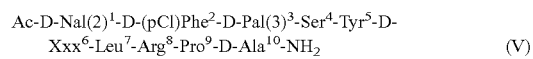
(V)

in which D-Xxx is an amino acid group of the general formula (VI)

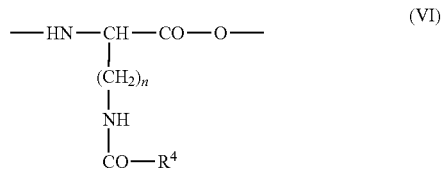
(VI)

in which n is the number 3 or 4, $R^4$ is a group of the formula (II)

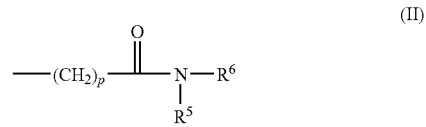
(II)

in which p is an integer from 1 to 4, $R^5$ is hydrogen or an alkyl group and $R^6$ is an unsubstituted or substituted aryl group or heteroaryl group, or $R^4$ is a ring of the general formula (III)

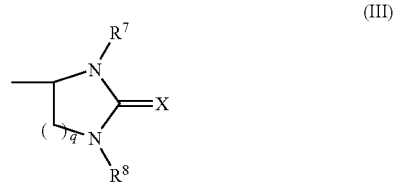
(III)

in which q is the number 1 or 2, $R^7$ is a hydrogen atom or an alkyl group, $R^8$ is a hydrogen atom or an alkyl group and X is an oxygen or sulphur atom, and its salts with pharmaceutically acceptable acids; and

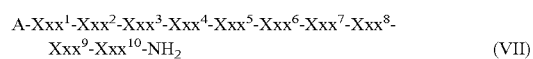
(VII)

in which

A is an acetyl or a 3-(4-fluorophenyl)propionyl group, $Xxx^1$ is D-Nal(1) or D-Nal(2), $Xxx^2$-$Xxx^3$ is D-Cpa-D-Pal(3) or a single bond, $Xxx^4$ is Ser, $Xxx^5$ N-Me-Tyr, $Xxx^6$ is D-Cit, D-Hci or a D-amino acid group of the general formula (VIII)

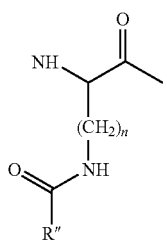

$$\text{(VIII)}$$

in which n is the number 3 or 4, where $R^{11}$ is a group having the general formula (IX)

where p is an integer from 1 to 4, $R^{12}$ is hydrogen or an alkyl group and $R^{13}$ is an unsubstituted or substituted aryl group or heteroaryl group, or $R^{11}$ is a 3-amino-1,2,4-triazole-5-carbonyl group or $R^{11}$ is a ring of the general formula (X)

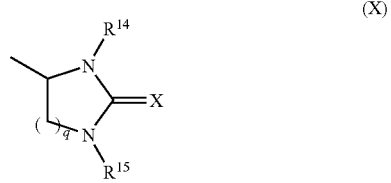

in which q is the number 1 or 2, $R^{14}$ is a hydrogen atom or an alkyl group $R^{15}$ is a hydrogen atom or an alkyl group and X is an oxygen or sulphur atom, $Xxx^7$ is Leu or Nle, $Xxx^8$ is Arg or Lys(iPr), $Xxx^9$ is Pro and $Xxx^{10}$ is Ala or Sar, and their salts with pharmaceutically acceptable acids.

EXAMPLE 1

By means of polarization microscopy, aggregation investigations were carried out on solutions of various cetrorelix salts without or with addition of excipients.

In the polarization light microscope with crossed polarizers, aggregated peptide solutions show images which are very similar to those of liquid-crystalline structures. In contrast to this, aggregate-free peptide solutions produce no such effects.

TABLE 1

Influence of a gluconic acid addition on the aggregation behaviour of cetrorelix acetate solutions.

| Concentration of cetrorelix acetate, mg/ml | Gluconic acid in the reconstitution medium, %: | pH | Days without aggregation |
|---|---|---|---|
| 2.5 | 0 | 4.7 | 1 |
| 2.5 | 0.0071 | 4.5 | 2 |
| 2.5 | 0.071 | 3.7 | 2 |
| 2.5 | 0.71 | 3.1 | 12 |

Thus the addition of gluconic acid causes an improvement in the stability of cetrorelix acetate solutions by delaying or preventing aggregation.

Further experiments concentrated on cetrorelix gluconate without or with addition of gluconic acid. The most important results are summarized in Table 2.

TABLE 2

Aggregation behaviour of various solutions which were prepared from cetrorelix gluconate bulk material.

| Concentration of cetrorelix, mg/ml | Gluconic acid addition: | | | |
|---|---|---|---|---|
| | Yes | | No | |
| | pH | Days without aggregation | pH | Days without aggregation |
| 2.5 | 3.0 | >30 | | |
| 5 | 3.6 | 4 | 4.8 | 1 |
| 5 | 3.8 | 4 | 4.7 | 1 |
| 7.5 | 3.4 | 1 | 4.7 | 0 |
| 7.5 | 3.7 | 1 | 4.8 | 0 |

Cetrorelix gluconate thus offers advantages in comparison with the acetate salt. The addition of gluconic acid increases the shelf life of cetrorelix gluconate solutions.

Moreover, the stabilizing influence of glucuronic acid on cetrorelix acetate solutions and, as a further salt, also cetrorelix glucuronate, was tested for its aggregation behaviour. The results are summarized in Table 3.

TABLE 3

Aggregation behaviour of variously concentrated solutions of cetrorelix acetate and cetrorelix glucuronate without or with addition of glucuronic acid.

| Salt form | Concentration of cetrorelix, mg/ml | Glucuronic acid addition: | | | |
|---|---|---|---|---|---|
| | | Yes | | No | |
| | | pH | Days without aggregation | pH | Days without aggregation |
| Acetate | 2.5 | 3.0 | >21 | 4.7 | 0 |
| Acetate | 5 | 3.0 | 0 | | |
| Glucuronate | 2.5 | 2.9 | >30 | 4.5 | 3 |
| Glucuronate | 5 | 2.7 | >30 | 4.6 | 0 |

Also, by the replacement of the acetate salt by a glucuronate salt, significant improvements can be achieved with respect to the aggregation stability of cetrorelix similarly to with the gluconate salt. By the addition of glucuronic acid to cetrorelix glucuronate solutions, the aggregation stability of these solutions can be even further improved.

TABLE 4

Aggregation-free duration in days of cetrorelix acetate solutions after addition of 10% of α-cyclodextrin, 20% of hydroxypropyl-β-cyclodextrin or 20% of γ-cyclodextrin.

| Concentration of cetrorelix acetate, mg/ml | α-Cyclo-dextrin | Hydroxypropyl-β-cyclodextrin | γ-Cyclodextrin |
|---|---|---|---|
| 2.5 | 7 | 24 | 98 + (168, 182, 189) |
| 5 | 0 | 7 | 31 + (140, 147, 182) |
| 7.5 | 0 | 10 | 5 + (20, 20, 20) |
| 10 | 0 | 2 | 2 + (4, 4, 4) |
| 15 | 0 | 0 | |

By the addition of hydroxypropyl-β-cyclodextrin and particularly of γ-cyclodextrin, the aggregation stability of cetrorelix acetate solutions can be significantly improved.

TABLE 5

Aggregation-free duration in days of 2.5 mg/ml cetrorelix gluconate solutions after addition of α-cyclodextrin, hydroxypropyl-β-cyclodextrin or γ-cyclodextrin.

| Cyclodextrin type | Concentration of cyclodextrin, % | Days without aggregation |
|---|---|---|
| γ-Cyclodextrin | 20 | 182 |
| | 6.8 | 126 |
| Hydroxypropyl-β-cyclodextrin | 20 | 189 |
| | 6.8 | 91 |
| α-Cyclodextrin | 10 | 140 |
| | 5 | 1 |

By the addition of hydroxypropyl-β-cyclodextrin or of γ-cyclodextrin, the aggregation stability of cetrorelix gluconate solutions can also be significantly improved.

TABLE 6

Aggregation-free duration in days of cetrorelix acetate solutions with addition of polyvinylpyrrolidone (Kollidon ® 12 PF or 17 PF).

| Concentration of cetrorelix, mg/ml | Concentration of Kollidon ®, % | Days without aggregation with Kollidon ® 12 PF | Days without aggregation with Kollidon ® 17 PF |
|---|---|---|---|
| 2.5 | 0 | 0 | 0 |
| | 5 | 1 | 2 |
| | 10 | 1 | 2 |
| | 15 | 77 | 63 |
| | 20 | 84 | 98 |
| 5 | 15 | 0 | 1 |
| | 20 | 0 | 1 |

Also, by the addition of various types of polyvinylpyrrolidone, the aggregation stability of cetrorelix acetate solutions can be significantly improved.

TABLE 7

Aggregation behaviour of cetrorelix acetate solutions with addition of various excipients assessed by means of polarization microscopy and according to the optical appearance.

| Excipient | Conc. of excipient | Conc. of cetrorelix | Aggregation (microscopy) | Appearance |
|---|---|---|---|---|
| Solutol ® HS 15 | 5.00% | 2.5 mg/ml | yes, after 14 days | clear solution |
| | 10.00% | 2.5 mg/ml | ≧112 days without aggregation | clear solution |
| | 20.00% | 2.5 mg/ml | ≧112 days without aggregation | clear solution |
| Cremophor ® EL | 5.00% | 2.5 mg/ml | yes, after 10 days | clear solution |
| | 10.00% | 2.5 mg/ml | ≧112 days without aggregation | clear solution |
| | 20.00% | 2.5 mg/ml | ≧112 days without aggregation | clear solution |
| | 20.00% | 5 mg/ml | yes, after 1 day | clear, viscose |
| L-glutamic acid | 0.80% | 2.5 mg/ml | yes, after 2 days | clear solution, pH 3.8 |
| Glucaric acid | 2.50% | 2.5 mg/ml | ≧12 days without aggregation | clear solution, pH 2.5 |
| Galacturonic acid | 2.50% | 2.5 mg/ml | ≧12 days without aggregation | clear solution, pH 2.6 |

EXAMPLE 2

Cetrorelix bulk material is dissolved in a concentration of 10 mg/ml in 30% strength acetic acid and diluted with an aqueous solution of the additives to a final concentration of 1 mg/ml of peptide in 3% acetic acid. This solution is then sterile-filtered and lyophilized (5 mg per vial).

After reconstitution of these lyophilizates, the solutions (2.5 mg/ml of cetrorelix) are investigated in the following tests for aggregate formation and release behaviour:

Polarization microscopy (pol. mic.): days without aggregation.

Filterability in %:

Cetrorelix solutions are prepared according to a standardized procedure and filtered through 0.22 μm or 0.45 μm filters by means of centrifugation. The concentration of cetrorelix in the filtrate is determined by HPLC and indicated as a % value, based on the starting concentration before filtration (filterability in %).

in-vitro release form (RRS, release in Ringer's solution): % released after 1 h and after 6 h.

The in-vitro release behaviour is determined at 37° C. in a flow procedure using Ringer's solution as medium. The concentration measurement is carried out by HPLC. Cetrorelix samples, corresponding to 10 mg of cetrorelix base, are weighed into the flow cell, mixed with 4 ml of water and stirred for 10 min. After addition of 6 ml of Ringer's solution to the sample, Ringer's solution is pumped uniformly through the flow cell with a flow of 0.5 ml/min, with stirring.

Rat animal experiment: cetrorelix residual content in the muscle in % of the administered dose 168 h after injection.

Some prepared batches of cetrorelix acetate lyophilizate and the corresponding test results of 2.5 mg/ml cetrorelix acetate solutions prepared therefrom are shown in Table 8a.

TABLE 8a

| Batches of cetrorelix acetate lyophilizate (5 mg) . . . Excipients | Pol.mic., days without aggr. | 0.22 μm filter-able [%] | RRS, [%] after 1 h | RRS, [%] after 6 h | Rat % i.m. after 168 h |
|---|---|---|---|---|---|
| only mannitol (= control) | 0 | — | | | about 55 |
| Solutol ®/mannitol | 48 | 100 | | | |
| Cremophor ®/mannitol | 46 | 101 | | | |
| Solutol ®/alanine | 16 | 98 | 17 | 24 | |
| Solutol ®/alanine/gluconic acid | 19 | 101 | 57 | 68 | 5.7 |
| Solutol ®/mannitol/gluconic acid | >45 | 100 | 84 | 88 | 3.8 |
| Cremophor ®/mannitol/gluconic acid | >45 | 101 | | | |
| Solutol ®/tryptophan/mannitol | imposs. | | | | |
| Solutol ®/tryptophan/gluconic acid | 6 | | | | 9.6 |
| Cyclodextrin molar ratio 1:10/mannitol | 2 | 101 | 16 | 27 | 10 |
| Cyclodextrin molar ratio 1:10/mannitol/gluconic acid | >45 | 102 | 68 | 74 | |
| Cyclodextrin molar ratio 1:30/mannitol | 17 | 100 | 68 | 76 | |
| Cyclodextrin molar ratio 1:10/alanine/gluconic acid | 5 | 101 | 39 | 52 | 6.3 |
| Mannitol/citric acid | 1 | 102 | 45 | 53 | |
| Solutol ®/mannitol/citric acid | >36 | 100 | 84 | 91 | 7.4 |
| Solutol ®/alanine/citric acid | 1 | 99 | 47 | 54 | |
| Solutol ®/glycine | >36 | 97 | 24 | 31 | |
| Solutol ®/urea | 21 | 100 | 32 | 40 | |
| Solutol ®/glycine/gluconic acid | >36 | 99 | 82 | 89 | |
| Solutol ®/urea/gluconic acid | >36 | 100 | | | |
| Cremophor ®/alanine/gluconic acid | (36) | | | | |
| Cremophor ®/urea/gluconic acid | (36) | | | | |
| Pluronic ® F127/mannitol | 1 | | | | |
| 5% Tween ® 80/mannitol | >16 | | | | |
| Polyethylene glycol 4000/mannitol | 1 | | | | |
| Dextran/mannitol | 1 | | | | |
| Phenylmercury acetate/mannitol | 2 | | | | |

In the examples shown, it is evident that with a large number of the tested excipients from various groups of substances (surface-active substances, acids, amino acids, polymers, sugars, sugar alcohols, cyclodextrins, preservatives), stabilizing effects can be achieved in vitro (polarization microscopy, filterability, in-vitro release) and in vivo individually or with mixtures of these excipients. This reduced tendency to aggregate and thus improved in-vitro release of active compound also leads in the rat experiment to improved bioavailabilies of the peptide active compound and thus to reduced residual contents in the rat muscle.

Further in-vitro and in-vivo data of batches containing various cetrorelix salts without or with addition of stabilizing excipients are listed in Table 8b which follows:

TABLE 8b

| Cetrorelix salts (reconstituted with water) Excipients | Conc. of cetrorelix from lyo mg/ml | Pol. mic days with-out aggr. | RRS, [%] after 1 h | RRS, [%] after 6 h | Rat % i.m. after 168 h |
|---|---|---|---|---|---|
| Acetate | 2.5 | 0 | 12 | 24.5 | about 55 |
| Acetate | 2.5 | 0 | 13 | 35.9 | about 55 |
| Acetate | 5 | 0 | 10 | 35 | |
| Acetate reconstituted with gluconic acid | 2.5 | 18 | 50 | 63.2 | 15.2 |
| Acetate + Kollidon ® 12 PF | 2.5 | 84 | 15 | 43.4 | 20.2 |
| Acetate + Kollidon ® 17 PF | 2.5 | 98 | 22 | 50.6 | |
| Acetate + benzalkonium chloride | 2.5 | | 6.3 | 30.3 | |
| Acetate + phospholipids | 2.5 | | 7.3 | 23.3 | |
| Acetate + γ-cyclodextrin (1:10) | 2.5 | | 22.6 | 44.5 | 10 |
| Acetate + γ-cyclodextrin (1:30) | 2.5 | | 28 | 56.7 | |
| Acetate + γ-cyclodextrin (1:50) | 2.5 | | 35.1 | 56.6 | |
| Acetate + γ-cyclodextrin (1:90) | 2.5 | >168 | 34.5 | 60.2 | 3.6 |
| Acetate + γ-cyclodextrin (1:90) | 5 | 140 | 19 | 47.8 | |
| Acetate + γ-cyclodextrin (1:90) | 7.5 | 20 | | | |
| Acetate + γ-cyclodextrin (1:90) | 10 | 4 | | | 45.2 |
| Acetate reconstituted with gluconic acid | 15 | | | | 49.1 |
| Gluconate | 2.5 | | 18 | 45.3 | |
| Gluconate | 2.5 | | 11.3 | 46 | |
| Gluconate reconstituted with gluconic acid | 2.5 | | 77.5 | 83.6 | |
| Citrate | 15 | | 9 | 20.3 | |
| Lactate | bulk | | 20 | 55.2 | |
| Embonate | 15 | | 13 | 43 | |

EXAMPLE 3

Cetrorelix formulations which are less prone/slower to aggregate (better filterability/polarization microscopy) and exhibit more rapid in-vitro release in Ringer's solution precipitate after 168 h in the rat muscle experiment owing to their lower residual content of cetrorelix. A higher bioavailability is expected of such formulations.

Some results of rat muscle experiments have already been listed in Tables 8a and 8b.

In the further rat muscle experiments shown in Table 9, in addition to the residual content in the muscle, the cetrorelix content in the plasma was additionally determined. With the aid of these data too, the stabilizing influence of the excipients tested is clear.

Moreover, it was possible by the replacement of the acetate salt by other salt forms of cetrorelix to achieve an improved bioavailability and, accompanying this, a reduced residual amount in the rat muscle experiment.

TABLE 9

| Substance (cetrorelix) | Dose (mg/kg) | Cetrorelix concentration of the inj. soln (mg/ml) | Cetrorelix content in the muscle (168 h), % of the dose | Cetrorelix content in the plasma, % of the dose |
|---|---|---|---|---|
| Acetate + Solutol ® + alanine + gluconic acid | 1.5 | 2.5 | 5.7 | |
| Acetate + Solutol ® + tryptophan + gluconic acid | 1.5 | 2.5 | 9.6 | |
| Acetate + cyclodextrin 1:10 | 1.5 | 2.5 | 10.0 | 83.4 |
| Acetate + cyclodextrin 1:10, alanine, gluconic acid | 1.5 | 2.5 | 6.3 | 81.8 |
| Acetate + Solutol ® + gluconic acid | 1.5 | 2.5 | 3.8 | |
| Acetate + Solutol ® + citric acid | 1.5 | 2.5 | 7.4 | |
| Acetate | 1.5 | 3 | 55.1 | 92.2 |
| Acetate in Miglyol ® | 1.5 | 3 | 22.3 | 74.2 |
| Acetate + benzalkonium chloride | 1.5 | 3 | 76.9 | 39.8 |
| Acetate + 20% cyclodextrin | 1.5 | 3 | 3.6 | 106.2 |
| Acetate + 20% Kollidon ® | 1.5 | 3 | 20.2 | 88.4 |
| Acetate + glucuronic acid | 1.5 | 3 | 23.6 | 106.1 |
| Acetate + gluconic acid | 1.5 | 3 | 15.2 | 95.5 |
| Acetate + 20% cyclodextrin | 3.0 | 10 | 45.2 | 60.9 |
| Acetate | 3.0 | 15 | 56.5 | 28.7 |
| Acetate in Miglyol ® | 3.0 | 15 | 24.2 | 57.2 |
| Acetate + 0.025% benzalkon. | 3.0 | 15 | 10.5 | 21.4 |
| Acetate + glucuronic acid | 3.0 | 15 | 78.1 | 43.8 |
| Acetate + gluconic acid | 3.0 | 15 | 49.1 | 45.5 |
| Gluconate | 1.5 | 15 | 37.9 | 46.9 |
| Gluconate in mannitol | 1.5 | 3 | 24.6 | 58.0 |
| Gluconate in mannitol | 1.5 | 3 | 25.4 | 75.2 |
| Gluconate in Miglyol ® | 1.5 | 3 | 28.8 | 46.3 |
| Gluconate in gluconic acid | 1.5 | 3 | 13.2 | 120.0 |
| Gluconate in gluconic acid | 3.0 | 15 | 29.2 | |
| Gluconate in gluconic acid | 3.0 | 15 | 43.5 | 74.2 |
| Glucuronate | 1.5 | 3 | 16.5 | 78.6 |
| Glucuronate | 3.0 | 15 | 18.8 | |
| Lactate | 3.0 | 15 | 33.2 | 72.1 |
| Lactate | 1.5 | 3 | 30.7 | 67.1 |
| Citrate lyo/a | 1.5 | 3 | 22.8 | 36.6 |
| Citrate in Miglyol ® | 1.5 | 3 | 14.8 | 53.1 |
| Base | 1.5 | 3 | 27.2 | 122.2 |
| Base in Miglyol ® | 1.5 | 3 | 38.9 | 55.9 |
| Benzoate in mannitol | 1.5 | 3 | 34.2 | 32.7 |
| Benzoate in Miglyol ® | 1.5 | 3 | 33.1 | 21.1 |
| Phosphate | 1.5 | 3 | 32.9 | 22.6 |

The invention claimed is:

1. A pharmaceutical composition for parenteral administration, comprising:
   (a) a pharmaceutically effective amount of the peptidic LHRH antagonist salt cetrorelix acetate, in a concentration of 2.5 mg/ml total solution;
   (b) a pharmaceutically acceptable acid and % in total solution thereof, selected from the group consisting of gluconic acid of 0.00710%, 0.071, or 0.71%, or glucaric acid or galacturonic acid of 2.5%, wherein the pharmaceutically acceptable acid is present as free acid and is in an amount capable of imparting a pH of 2.5, 2.6, 3.1, 3.7, or 4.5 to the composition and suppressing aggregation of cetrorelix acetate; and
   (c) a carrier, wherein the carrier is water or an aqueous solvent mixture.

2. The pharmaceutical composition of claim 1, further comprising an excipient.

3. The pharmaceutical composition of claim 2, wherein the excipient comprises gluconic acid, glucuronic acid, galacturonic acid, glucaric acid, citric acid, ascorbic acid, or an amino acid.

4. The pharmaceutical composition of claim 2, wherein the excipient comprises polyethylene glycol 12(hydroxy)stearate (Solutol®), polyoxyethylene ricinoleate (Cremophor®), polysorbates, poloxamers, phospholipids, lecithins, or a preservative.

5. The pharmaceutical composition of claim 2, wherein the excipient comprises albumins, polyethylene glycols, cellulose derivatives, starch derivatives or polyvinylpyrrolidone.

6. The pharmaceutical composition of claim 2, wherein the excipient comprises cyclodextrins or its derivatives, or sugar alcohols.

7. The pharmaceutical composition of claim 2, wherein the excipient comprises urea or other chaotropic substances.

8. The pharmaceutical composition of claim 1, wherein the release of cetrorelix acetate is delayed by the use of a polymer.

9. The pharmaceutical composition of claim 8, wherein the Polymer is a homo- or copolymer of lactic or glycolic acid.

10. The pharmaceutical composition of claim 4, wherein the preservative is benzalkonium chloride or phenylmercury acetate.

11. The pharmaceutical composition of claim 6, wherein the sugar alcohol is mannitol.

12. The pharmaceutical composition of claim 1, wherein the pharmaceutical composition for parenteral administration is an injection preparation.

13. The pharmaceutical composition of claim 12, wherein the injection preparation is for subcutaneous injection.

14. The pharmaceutical composition of claim 2, wherein the excipient is independently selected from mannitol, polyethylene glycol 12-(hydroxyl)stearate, polyoxyethylene ricinoleate, glycine, citric acid and cyclodextrin.

15. The pharmaceutical composition of claim 1 manufactured by reconstitution of a lyophilisate of the cetrorelix acetate, wherein the reconstitution medium is water containing a pharmaceutically acceptable acid independently selected from gluconic acid or galacturonic acid.

16. The pharmaceutical composition of claim 1 manufactured by reconstitution of a lyophilisate of cetrorelix acetate, wherein the reconstitution medium is water containing a pharmaceutically acceptable acid independently selected from gluconic acid, glucaric acid and galacturonic acid.

17. The pharmaceutical composition of claim 1 manufactured by reconstitution of a lyophilisate consisting of the Cetrorelix salt and an excipient independently selected from mannitol, polyethylene glycol 12- (hydroxyl)stearate, polyoxyethylene ricinoleate, glycine, citric acid and cyclodextrin, wherein the reconstitution medium is water containing a pharmaceutically acceptable acid independently selected from gluconic acid, glucaric acid and galacturonic acid.

* * * * *